US00PP35048P2

(12) United States Plant Patent
Westervelt

(10) Patent No.: US PP35,048 P2
(45) Date of Patent: Mar. 21, 2023

(54) NORWAY SPRUCE TREE NAMED 'ANDY SPINKS'

(50) Latin Name: *Picea abies*
Varietal Denomination: 'Andy Spinks'

(71) Applicant: Keith D. Westervelt, Manhattan, KS (US)

(72) Inventor: Keith D. Westervelt, Manhattan, KS (US)

( * ) Notice: Subject to any disclaimer, the term of this patent is extended or adjusted under 35 U.S.C. 154(b) by 0 days.

(21) Appl. No.: 17/728,083

(22) Filed: Apr. 25, 2022

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — Susan McCormick Ewoldt
(74) *Attorney, Agent, or Firm* — Penny J Aguirre

(57) ABSTRACT

A new cultivar of Norway spruce tree named 'Andy Spinks' that is characterized by its new and maturing foliage that is golden-tinted in color with older and shaded foliage blue-green in color, its strong central leader, its very uniform growth habit and shape, and its good growth rate.

1 Drawing Sheet

Botanical classification: *Picea abies.*
Varietal denomination: 'Andy Spinks'.

BACKGROUND OF THE INVENTION

The present invention relates to a new and distinct cultivar of *Picea abies* and will be referred to hereafter by its cultivar name, 'Andy Spinks'. 'Andy Spinks' represents a new hybrid of Norway spruce, an evergreen plant grown for landscape use.

The inventor discovered 'Andy Spinks' as a naturally occurring branch mutation in March of 2007 on an unnamed and unpatented plant of *Picea abies* growing in a home landscape in Portland, Oreg.

Asexual propagation of the new cultivar was first accomplished by grafting onto rootstock of *Picea abies* in McMinnville, Oreg. in January of 2020 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Andy Spinks' as a unique cultivar of *Picea.*

1. 'Andy Spinks' exhibits new and maturing foliage that is golden-tinted in color with older and shaded foliage blue-green in color.
2. 'Andy Spinks' exhibits a strong central leader.
3. 'Andy Spinks' exhibits a very uniform growth habit and shape.
4. 'Andy Spinks' exhibits a good growth rate.

The parent plant of 'Andy Spinks' differs from 'Andy Spinks' in having green needles. 'Andy Spinks' can be most closely compared to the cultivars 'Gold Drift' (not patented) and 'Golden Finch' (not patented). Both are similar to 'Andy Spinks' in being hardy in U.S.D.A. Zones 2 to 6 and in having gold tinted foliage. 'Golden Finch' is also similar to 'Andy Spinks' in having foliage that is also similar in shape and size. 'Gold Drift' and 'Golden Finch' both differ from 'Andy Spinks' in having a less uniform growth habit and more weeping plant habits. In addition, 'Golden Finch' differs from 'Andy Spinks' in having a more dwarf plant habit.

BRIEF DESCRIPTION OF THE DRAWING

The plant depicted in the accompanied photograph illustrates the characteristics of 'Andy Spinks'. The photograph was taken of a plant about 4 years in age as grown in the ground in Gresham, Oreg. and provides an overall view of the plant habit and foliage coloration of 'Andy Spinks'. The colors in the photograph is as close as possible with the photographic and printing technology utilized. The color values cited in the detailed botanical description accurately describes the colors of the new *Picea.*

DETAILED BOTANICAL DESCRIPTION

The following is a detailed description of the new cultivar as taken from 3-year-old trees as grown outdoors in 3-gallon containers in Manhattan, Kans. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Plant type.*—Coniferous evergreen.

*Growth habit.*—Upright, uniform.

*Height and spread.*—An average of 56 cm in height and 36 cm in width as a 3 year-old tree in a 3-gallon container, reaches 4.6 m in height with a spread of 1.2 m in spread as a 7-year-old plant in the landscape.

*Hardiness.*—At least in U.S.D.A. Zones 2 to 6 some leaf scorching can occur in zone 6).

*Diseases and pests.*—No susceptibility or resistance to pests or diseases has been observed.

*Root description*.—Fibrous, moderately branched, moderately thick, a blend of N199B and N199C in color.

*Growth rate*.—An average of 6 inches per year.

*Propagation*.—Grafting.

*Time to produce a young plant*.—6 to 8 weeks for graft to take after grafting onto understock of *Picea abies* in the winter.

Branch description:

*Trunk and branch shape*.—Rounded.

*Branch size*.—Main trunk; 37 cm in length, 2 cm in diameter, lateral branches; average of 8 cm in length, up to 7 mm in width, tertiary branches; up to 6.5 cm in length, 3 mm in width.

*Stem surface*.—Uniformly scabrous, densely covered with whorled scales, each is linear in shape up to 6 mm in length, 2 mm in width, and slightly raised off the stem surface, apex is acute sharply pointed and slightly curved outward apex holding a needle, base fused, overall appearance of stem is slightly sheen, trunk; rugose and exfoliating, dry, matte.

*Branching*.—1 main branch, 23 lateral branches, 2 to 4 tertiary per lateral branch.

*Stem arrangement*.—Lateral branches; irregularly whorled to opposite, tertiary branches; opposite.

*Stem aspect*.—Strong, held in a downward angle.

*Internode length*.—Average of 4 cm.

*Stem color*.—Main stem; 198A and 197A, apex tinged 199A, lateral stems 177B and 175A, trunk; N200B and N200A.

*Resin glands*.—None observed.

Foliage description:

*Leaf arrangement*.—Densely whorled needles, held outward from stem and slightly bending in similar pattern-like directions, en masse; bristly in appearance.

*Leaf attachment*.—Sessile.

*Leaf shape*.—Acicular, slightly flattened.

*Leaf division*.—Simple.

*Leaf base*.—Truncate.

*Leaf apex*.—Linear.

*Leaf venation*.—Slightly visible, parallel.

*Leaf margins*.—Entire.

*Leaf fragrance*.—When crushed, it produces a pine-like fragrance.

*Leaf surface*.—Upper and lower surfaces; glabrous, slightly glossy.

*Leaf color*.—New growth; 154A, base 144C, older needles; 139A.

*Leaf texture*.—Thick, typical evergreen type needle texture, strong.

*Leaf size*.—An average of 2 cm in length and 2 mm in width.

*Leaf quantity*.—Average of 280 per lateral branch.

*Leaf buds*.—1.5 cm in length and 8 mm in width, comprised of imbricate scales; orbicular and cupped in shape, whorled around immature shoot, both surfaces transparent and paper-like and 164A in color, base fused, apex acuminate cupping outward at burst, 3 mm in length, 2 mm in width, a paper-like casing drops after immature shoots burst; casing is an average of 1 cm in length and width, thin and transparent and closest to 161D in color, pointed triangular apex.

*Immature shoots*.—Average of 16 per lateral branch, 1.5 cm in length, 2 cm in width, whorled, appears overall circular in shape, held in a downward slightly drooping aspect, individual needles; soft, tender, glabrous, matte, acicular and rounded in shape, no venation, 1 mm in width, 1 cm in length, color; 144B, base 145C, scales dropped after shoots are fully open.

Cone description: No cones have been produced to date.

It is claimed:

1. A new and distinct cultivar of Norway Spruce tree named 'Andy Spinks' as herein illustrated and described.

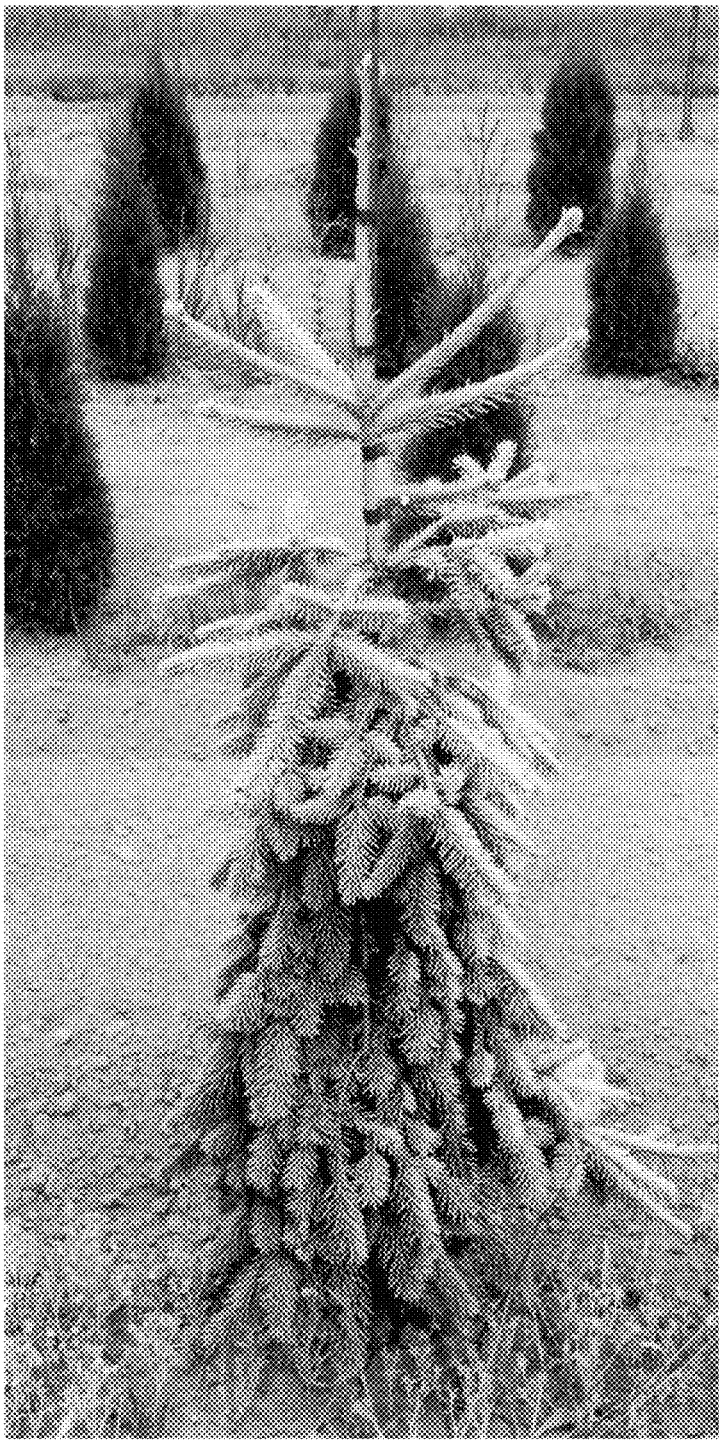

* * * * *